United States Patent [19]
Anderson et al.

[11] Patent Number: 5,453,418
[45] Date of Patent: Sep. 26, 1995

[54] RACTOPAMINE AND GROWTH HORMONE COMBINATIONS

[75] Inventors: David B. Anderson, Greenfield; D. Jay Jones, Indianapolis; Alvin L. Melliere, Greenfield, all of Ind.

[73] Assignee: Eli Lilly and Company, Indianapolis, Ind.

[21] Appl. No.: 984,192

[22] Filed: Nov. 20, 1992

Related U.S. Application Data

[63] Continuation of Ser. No. 694,628, May 2, 1991, abandoned, which is a continuation-in-part of Ser. No. 164,675, Mar. 7, 1988, abandoned.

[51] Int. Cl.$^6$ ............ A61K 31/05; A61K 31/135; A61K 38/25; A61K 38/27
[52] U.S. Cl. .................................. 514/12; 514/653
[58] Field of Search .............................. 514/12, 806, 653, 514/21

[56] References Cited

U.S. PATENT DOCUMENTS

| | | | |
|---|---|---|---|
| 4,522,822 | 6/1985 | Kiernan | 514/376 |
| 4,690,951 | 9/1987 | Anderson et al. | 514/653 |
| 4,792,546 | 12/1988 | Baker | 514/523 |
| 4,977,825 | 3/1991 | Wagner | 514/171 |

FOREIGN PATENT DOCUMENTS 0511003 10/1992 European Pat. Off. .

OTHER PUBLICATIONS

Hohmann, K. "One Giant Step for the Pork Industry", *Hog Farm Management*, pp. 8–13, 29 (Oct. 1986).
Kim, Y. S. et al., "Effect of the Repartitioning Agent Cimaterol on Growth, Carcass & Skeletal Muscle Characteristics in Lambs", *J. Anim. Sci.*, vol. 65, No. 5, 1392–1399 (1987).
Moser, R. L. et al., "Effect of Cimaterol (CL263780) as a Repartitioning Agent In the Diet for Finishing Pigs", *J. Anim. Sci.*, vol. 62, 21–26 (1986).
Mersmann, H. J. et al., "Growth & Adipose Tissue Metabolism in Young Pigs Fed Cimaterol with Adequate or Low Dietary Protein", *J. Anim. Sci.*, vol. 64, No. 5 1384–1394 (1987).
Anderson, D. B. et al., "The Effect of Dietary Protein on Nitrogen Metabolism, Growth Performance & Carcass Composition of Finishing Pigs Fed Ractopamine", *Federation Proceedings*, Federation of American Scoieties for Experimental Biology, vol. 46, No. 4, 1021, (Mar. 5, 1987).
Welsh, T. H., Jr. et al., "Growth Hormone Releasing Factor & Clenbuterol Regulation of Bovine Growth Hormone Secretion In Vitro", *J. Anim. Sci.*, vol. 65, Suppl. 1, 279 (1987).
Williams, P. E. V. et al., "The Effects of a Combination of the B–Agonist Clenbuterol & Bovine Pituitary Growth Hormone on Growth of Milk–Fed Calves", *Animal Production*, vol. 44, Part 3, 475 (1987).
James, S. et al., "Effect of Clenbuterol on the Growth & Carcass Composition of Hypophysectomized Rats in the Presence or Absence of Growth Hormone", *Proc. of the Nutrition Soc.*, vol. 46, No. 2, 108A (1987).
*Endocrinology*, 1991, vol. 129, #1, pp. 465–474.
*Animal Production* 44, #3, 475 (Jun. 1987).
*Proc. of the Nutrition Soc.*, 46, #2, 108 A (1987).
*Endocrinology*, 122, #2, 531 (1988).
*J. Endocrinology*, 115, Suppl., #68 (1987).
*Fed. Proc.* 45 (4), 1096 (1986).
*J. Animal Science*, vol. 67, Supplement 1 and *J. Dairy Science*, vol. 72, Supplement 1—#544 and 545 (Jul. 31–Aug. 4, 1989).
*J. Anim. Sci.*, 35(4), 794–800 (1972).
Federation Proceedings, 46, #3, abstract 4104 (p. 1021) Mar. 1, 1987.

*Primary Examiner*—Jeffrey E. Russel
*Attorney, Agent, or Firm*—Kathleen R. S. Page

[57] ABSTRACT

Combined administration of a growth hormone related substance and ractopamine, cimaterol, clenbuterol, L-644,969, or albuterol to swine provides improved growth feed efficiency, and carcass quality. Administration of ractopamine, cimaterol, clenbuterol, L-644,969, or albuterol to swine that also receive growth hormone related substance reduces greater than normal blood sugar and insulin levels.

12 Claims, No Drawings

RACTOPAMINE AND GROWTH HORMONE COMBINATIONS

This application is a continuation of application Ser. No. 07/694,628, filed May 2, 1991, now abandoned, which is a continuation-in-part of application Ser. No. 07/164,675, filed Mar. 7, 1988, now abandoned.

CROSS REFERENCE TO RELATED APPLICATION

BACKGROUND OF THE INVENTION

This invention provides a combination product useful for improving feed efficiency, growth rate, and carcass quality of pigs. It also provides related growth promotion methods.

Ractopamine and its use as a growth promoter for pigs are disclosed in U.S. Pat No. 4,690,951.

Growth hormone and growth hormone related substances are also recognized growth promoters for pigs. *J. Anim. Sci.* 35 (4), 794–800 (1972). However, certain disadvantages accompany use of exogenously administered growth hormone and growth hormone related substances. More specifically, the ratio of carcass weight to live weight (dressing percent) is reduced when growth hormone is used. This arises because growth hormone increases rate of viscera growth faster than it increases rate of carcass (muscle, bone, skin, and fat) growth. Further, use of growth hormone causes increased blood sugar and insulin levels which can be detrimental to the health of the pigs.

SUMMARY OF THE INVENTION

The present invention provides a composition comprising a growth hormone related substance in combination with ractopamine, cimaterol, clenbuterol, L-644,969, or albuterol.

The invention also provides a method of improving growth, feed efficiency, or carcass quality of a pig which comprises administering both a growth hormone related substance and ractopamine, cimaterol, clenbuterol, L-644,969, or albuterol to the pig.

The invention also provides a method of reducing a greater than normal blood sugar level in a pig that has received a dose of growth hormone related substance, which comprises administering ractopamine, cimaterol, clenbuterol, L-644,969, or albuterol to the pig.

DETAILED DESCRIPTION OF THE INVENTION

Ractopamine is the generic name for 4-hydroxy-α-[[[-3-(4-hydroxyphenyl)-1-methylpropyl]amino]methyl]benzenemethanol. Preparation of this compound, its salts and congeners, and their use as growth promoters are disclosed in U.S. Pat. No. 4,690,951. The term "ractopamine" as used herein refers not only to the free base, but also to acid addition salts thereof. Ractopamine can be administered by either an oral or parenteral route.

Abuterol is the generic name for α-[[(1,1-dimethylethyl)amino]methyl]-4-hydroxy-1,3-benzenedimethanol. Preparation of this compound is disclosed in U.S. Pat. No. 3,644,353.

Cimaterol is the generic name for 2-amino-5-[1-hydroxy-2-[(1-methylethyl)amino]ethyl]benzonitrile. Preparation of this compound is disclosed in U.S. Pat No. 4,522,822.

Clenbuterol is the generic name for 4-amino-3,5-dichloro-α-[[(1,1-dimethylethyl)amino]methyl]benzenemethanol. Preparation of this compound is disclosed in U.S. Pat. No. 3,536,712.

L-644,969 is a recognized code designation for 6-amino-α-[[(1-methyl-3-phenylpropyl)amino]methyl]-3-pyridinemethanol dihydrochloride (R,R), as indicated in *Reciprocal Meat Conference Proceedings*, Vol. 40, p. 47 (1987).

The term "growth hormone related substance" includes growth hormone (somatotropin), growth hormone releasing factor, somatomedin, or any substance that stimulates the production of endogenous growth hormone and the production of somatomedin. Substances that stimulate endogenous growth hormone include enkephalins or enkephalin-like compounds, prostaglandins, alpha-adrenergics, benzodiazapines, barbiturates, opiate antagonists, gamma-aminobutyric acid (GABA), GABAergic compounds, and the like. Other substances that can be administered include any analogues of growth hormone or growth hormone releasing factor such as methionyl bovine growth hormone, 29 amino acid growth hormone releasing factor, and the like. Administration of growth hormone can also be achieved by implanting cells which produce growth hormone for example, pituitary tumor cells, or cells which produce growth hormone releasing factor.

The growth hormone related substance can be a natural or recombinant product, or it can be prepared by solid-phase synthetic procedures. In addition, the growth hormone or related substance need not be species specific. For example, porcine, bovine, or human growth hormone can be used in the administration of growth hormone to pigs.

Due to the protein nature of the growth hormone related substances, it is not desirable to administer it in an oral form. Intramuscular, intravenous, or subcutaneous injections can be used; also the growth hormone related substance can be delivered from an implant.

In accordance with the growth promotion methods provided by the invention, the ractopamine, cimaterol, clenbuterol, L-644,969, or albuterol, and the growth hormone related substance may be administered either separately or in combined form. When administered separately, the growth hormone related substance will typically be administered parenterally, and the ractopamine, cimaterol, clenbuterol, L-644,969, or albuterol will be delivered orally, e.g. in the animal's feed, but can also be delivered parenterally.

The compositions of the invention, which contain both the growth hormone related substance and ractopamine, cimaterol, clenbuterol, L-644,969, or albuterol, will typically be combined with a carrier to enable parenteral delivery of the combination. A suitable carrier for parenteral injection, for example, is 0.2M potassium phosphate buffer.

In addition, the composition may be administered by implant, or by other drug delivery devices, such as microcapsules, pumps, and the like.

The amounts of the substances to be employed in the present invention will vary and are not critical so long as the amounts are effective. In general, the present invention contemplates that 0.05 to 100 mg/head/day of ractopamine, cimaterol, clenbuterol, L-644,969, or albuterol, and 0.5 to 10 mg/head/day of porcine growth hormone will be delivered to swine. Preferably, the amount of ractopamine delivered is in the range of 0.25 to 60 mg/head/day. The preferred amount of porcine growth hormone is 1.5 to 6.0 mg/head/day. Accordingly, compositions of the invention should contain ractopamine and pGH in a weight ratio of from about 0.25/3 to 60/1.5.

It will be understood that daily administration is not necessary, and that the recommended amounts are averages. Thus, biweekly injections may be used, for example. If implants are used, administration may be semiweekly, or at even greater intervals. If administered in the feed, an appropriate amount of ractopamine is 1 to 30 ppm, preferably 2.5 to 20 ppm.

The amount of protein in the diet of treated animals is an important consideration. Typical feed rations for finishing pigs (i.e., those weighing from about 75 lbs to market weight) contain about 13% to 16% protein. If swine weighing 75 lbs and up receive porcine growth hormone and a diet that contains only 13% to 16% protein, however, then little additional improvement in growth rate is observed if ractopamine is also administered. In accordance with one aspect of this invention, the diet protein level should be greater than 16%, preferably above 18%, and more preferably 20% or above. These higher protein levels can also be achieved by supplementing lower protein diets with the limiting amino acids to make them equivalent to higher protein level diets. Then the additional administration of ractopamine to an animal receiving porcine growth hormone does provide an additive increase in growth rate.

As demonstrated in the following experimental results, simultaneous treatment with both growth hormone and ractopamine improves carcass parameters, including dressing percent, percent fat-free muscle, loin eye area, and leanness. These advantages are obtained even with the diet containing the lower levels of crude protein.

The results also show that combined treatment reduces blood glucose and insulin levels compared to those observed when pigs are treated with pGH alone.

EXPERIMENT 1

This experiment evaluated the effect of separate or combined treatment of finishing swine with pGH and ractopamine. In this case the diet contained a calculated 16.68% crude protein. Barrows and gilts, weighing an average of about 61.2 kg, were allocated to four treatment groups. The first group was the control group. The second group of animals received daily subcutaneous injections of pGH (in sterilized 0.2M potassium phosphate buffer); for the first 28 days, each animal received 3 mg/day, and thereafter until the end of the trial, each animal received 4 mg/day. A third group of animals received ractopamine at a rate of 10 ppm in their feed. The fourth group received both daily subcutaneous injections of pGH and ractopamine in their feed at 10 ppm; the pGH was supplied in the amount of 3 mg/day for the first 28 days and in the amount of 4 mg/day thereafter until the end of the trial. The first and third groups also received daily injections of 0.2M potassium phosphate buffer solution.

The feed ration used was the following:

| INGREDIENT | PERCENT |
| --- | --- |
| Corn, Yellow, Ground | 76.70 |
| Soybean Oil Meal, Solvent Extracted, Dehulled, 50% | 19.35 |
| Calcium Carbonate | 1.20 |
| Dicalcium Phosphate, Feed Grade | 1.20 |
| Salt (NACl) | 0.50 |
| Other Ingredients (minerals + vitamins + methionine) | 1.05 |
| Total | 100.00 |

The animals continued on treatment for an average of 52 days. The following table gives a summary of observed results, The column headed "Feed/Gain" reports the "Average Daily Feed" divided by the "Average Daily Gain". The table shows that when a feed ration containing only 16.7% crude protein is used, the "Feed/Gain" ratio is not improved by combining ractopamine and pGH treatment. The column headed "Dressing %" reports the ratio of the average hot carcass weight to the average final live weight. It shows that by combining ractopamine and pGH treatment the reduction in dressing % observed with pGH treatment is reversed.

| Treatment Description | No. Pigs | Avg Days on Test | Total Animal Days | Avg Initial Weight (Kg) | Avg Final Weight (Kg) | Avg Gain (Kg) | Avg Daily Gain (Kg) | Total Feed (Kg) | Avg Daily Feed (Kg) | Feed/ Gain | Dress- ing % | 10th Rib Fat (cm) | 10th Rib Loin Eye Area (sq cm) | Est Fat- Free Muscle (%) |
| --- | --- | --- | --- | --- | --- | --- | --- | --- | --- | --- | --- | --- | --- | --- |
| Control | 15 | 54.5 | 817 | 60.3 | 103.7 | 43.2 | 0.79 | 2367 | 2.87 | 3.65 | 74.3 | 2.57 | 30.77 | 49.3 |
| pGH | 14 | 53.0 | 742 | 61.7 | 104.4 | 42.8 | 0.81 | 1911 | 2.57 | 3.18 | 73.0 | 2.31 | 33.23 | 51.1 |
| Ractopamine | 14 | 47.0 | 658 | 61.2 | 104.9 | 43.4 | 0.91 | 1876 | 2.81 | 3.09 | 74.3 | 2.44 | 34.97 | 51.4 |
| pGH + Ractopamine | 15 | 49.8 | 747 | 61.2 | 104.8 | 43.4 | 0.86 | 2018 | 2.69 | 3.12 | 74.0 | 2.21 | 36.65 | 62.9 |

EXPERIMENT 2

This experiment evaluated the effect of separate or combined treatment of finishing swine with pGH and ractopamine, with the diet containing 20% crude protein. Barrows, each weighing about 68 kg (149 lbs), were randomly allocated to four treatment groups. The first group was the control group. A second group of animals received daily 4 ml injections (i.m.) containing pGH (in 0.2M potassium phosphate buffer) at a rate of approximately 60 mcg/kg of body weight, which amounted to between 4 and 8 mg/head/day (dose adjusted every two weeks). A third group of animals received ractopamine at a rate of 10 ppm in their feed. The fourth group received daily 4 ml injections containing pGH at the rate of approximately 60 mcg/kg of body weight and ractopamine in their feed at 10 ppm. The first and third groups also received daily injections of 4 ml of 0.2M potassium phosphate buffer solution.

| INGREDIENT | PERCENT |
| --- | --- |
| Corn, Yellow, Ground (8% C.P.) | 58.31 |
| Soybean Oil Meal (48% C.P.) | 32.00 |
| Dicalcium Phosphate | 2.25 |
| Calcium Carbonate | 1.00 |
| Salt | 0.62 |
| Other Ingredients (minerals + vitamins) | 0.82 |
| Animal Fat | 5.00 |
|  | 100.00 |

The animals continued on treatment for an average of 60 days. The following table gives a summary of the observed results. Animals receiving combined treatment with pGH and ractopamine showed the highest daily gains, the best feed efficiency (lowest Feed/Gain), least fat, largest loin eye area, greatest percent fat-free muscle, and a dressing percent identical to controls.

| Treatment Description | No. Pigs | Avg Days on Test | Total Animal Days | Avg Initial Weight (Kg) | Avg Final Weight (Kg) | Avg Gain (Kg) | Avg Daily Gain (Kg) | Total Feed (Kg) | Avg Daily Feed (Kg) | Feed/ Gain | Dress- ing % | 10th Rib Fat (cm) | 10th Rib Loin Eye Area (sq cm) | Est Fat- Free Muscle (%) |
| --- | --- | --- | --- | --- | --- | --- | --- | --- | --- | --- | --- | --- | --- | --- |
| Control | 12 | 64.4 | 773 | 67.6 | 124.0 | 56.6 | 0.88 | 2403 | 3.11 | 3.56 | 74.1 | 3.58 | 34.32 | 47.5 |
| pGH | 12 | 58.7 | 704 | 67.6 | 126.7 | 59.1 | 1.01 | 2005 | 2.85 | 2.84 | 73.0 | 2.95 | 41.48 | 52.6 |
| Ractopamine | 10 | 59.6 | 596 | 67.6 | 124.8 | 57.2 | 0.94 | 1585 | 2.65 | 2.80 | 75.0 | 2.77 | 46.19 | 55.2 |
| pGH + Ractopamine | 11 | 55.7 | 613 | 67.1 | 123.7 | 56.4 | 1.02 | 1677 | 2.71 | 2.66 | 74.1 | 2.39 | 47.23 | 56.8 |

EXPERIMENT 3

Increased nitrogen retention or decreased urinary urea excretion is a good indicator of improved feed efficiency. This experiment evaluated the effect on urinary urea excretion of separate versus combined treatment with porcine growth hormone (pGH) and ractopamine when the diet contained 16% or 20% crude protein.

Twenty-four crossbred barrows, each weighing approximately 60 kg were acclimated to individual metabolism cages. For a period of one week, half of the animals received a diet containing 16.3% crude protein, and the other animals received a diet containing 20% crude protein. Then, three animals that were receiving the diet with 16.3% crude protein were allocated to each of four treatments: (1) control animals that continued to receive a diet containing 16.3% crude protein, (2) animals that continued to receive a diet containing 16.3% crude protein and also received daily subcutaneous injections of 3 mg of pGH (in 3 ml of sterilized 0.2M potassium phosphate buffer, pH 7.8), (3) animals that continued to receive a diet containing 16.3% crude protein and also received ractopamine at the rate of 20 ppm in their feed, (4) animals that continued to receive a diet containing 16.3% crude protein and also received both daily injections of 3 mg of pGH and 20 ppm of ractopamine in their feed; and three animals that were receiving the diet with 20% crude protein were allocated to each of four treatments, corresponding to the first four: (5) control animals that continued to receive a diet containing 20% crude protein, (6) animals that continued to receive a diet containing 20% crude protein and also received daily subcutaneous injections of 3 mg of pGH, (7) animals that continued to receive a diet containing 20% crude protein and also received ractopamine at the rate of 20 ppm in their feed, and (8) animals that continued to receive a diet containing 20% crude protein and also received both daily injections of 3 mg of pGH and ractopamine at the rate of 20 ppm in their feed. Animals in groups 1, 3, 5, and 6 also received daily subcutaneous injections of 0.2M potassium phosphate buffer.

The two feed rations used had the following compositions:

| 16.3% Crude Protein Ration | |
| --- | --- |
| INGREDIENT | PERCENT |
| Corn, Yellow, Ground (8% C.P.) | 74.75 |
| Soybean Oil Meal (48% C.P.) | 21.50 |
| Dicalcium Phosphate | 1.80 |

| -continued | |
| --- | --- |
| 16.3% Crude Protein Ration | |
| INGREDIENT | PERCENT |
| Calcium Carbonate | 0.80 |
| Salt | 0.50 |
| Other Ingredients (minerals + vitamins) | 0.65 |
|  | 100.00 |

| 20% Crude Protein Ration | |
| --- | --- |
| INGREDIENT | PERCENT |
| Corn, Yellow, Ground (8% C.P.) | 65.50 |
| Soybean Oil Meal (48% C.P.) | 30.75 |
| Dicalcium Phosphate | 1.80 |
| Calcium Carbonate | 0.80 |
| Salt | 0.50 |
| Other Ingredients (minerals + vitamins) | 0.65 |
|  | 100.00 |

The animals received treatment for nine days. Then treatment was discontinued, and thereafter the animals that had been fed the diet containing 16.3% crude protein, instead received the diet containing 20%. Similarly, the animals that had been fed the diet containing 20% crude protein, instead received the diet containing 16.3%. After a nine day adaptation period, treatment resumed, with each animal receiving the same treatment it had previously, except for the level of dietary protein, which was the opposite level from that which it received in the first treatment period. Treatment continued for nine days. Accordingly, a total of six animals received each of the eight treatments.

During the experiment, urine was collected, and the amount of nitrogen excreted in the urine was determined for each animal. The results of this experiment are reported in the following table, which shows that combined treatment of finishing swine with pGH andractopamine substantially reduced nitrogen excretion as compared to controls and separate treatment with one compound or the other, when the level of crude protein was 20%.

|  | Urinary Urea, g/day | | | |
| --- | --- | --- | --- | --- |
|  | No. Pigs | 16% Protein | No. Pigs | 20% Protein |
| Control | 6 | 21.0 | 6 | 28.7 |
| pGH (3 mg/day)[1] | 6 | 16.4 | 6 | 22.6 |
| ractopamine (20 ppm) | 6 | 16.5 | 6 | 21.6 |
| ractopamine + pGH[1] | 6 | 16.0 | 5 | 18.1 |

[1]3 mg in $KH_2PO_4$ carrier was injected S.Q. daily.

The levels of glucose and insulin in the blood were also measured. The results are reported in the following two tables.

|  | Glucose (mg/dl) | | | |
| --- | --- | --- | --- | --- |
|  | No. Pigs | 16% Protein | No. Pigs | 20% Protein |
| Control | 6 | 96.0 | 6 | 89.2 |
| pGH | 6 | 98.6 | 6 | 99.5 |
| ractopamine | 6 | 82.2 | 6 | 86.0 |
| ractopamine + pGH | 6 | 93.5 | 5 | 95.6 |

|  | Insulin (microunits/ml) | | | |
| --- | --- | --- | --- | --- |
|  | No. Pigs | 16% Protein | No. Pigs | 20% Protein |
| Control | 6 | 14.3 | 6 | 12.6 |
| pGH | 6 | 15.7 | 6 | 17.5 |
| ractopamine | 6 | 11.0 | 6 | 9.2 |
| ractopamine + pGH | 6 | 13.6 | 5 | 13.4 |

EXPERIMENT 4

Twenty crossbred barrows, each weighing approximately 175 pounds, maintained in individual metabolism cages, with an indwelling cannula surgically inserted into the femoral vein, were used to determine the effect of ractopamine on reducing the hyperglycemic and hyperinsulinemic activity of growth hormone. Five barrows were assigned to each of four groups, using a randomized block design, blocking on pretreatment insulin levels. One group was the control group. A second group received pGH (6 mg/day SQ). A third received ractopamine (20 ppm in feed). The fourth group received the combination of pGH (6 mg/day SQ) and ractopamine (20 ppm in feed). The pigs were accustomed to a feeding regime of 2000 g of feed per day, equally divided between two feedings. This was approximately 70–80% of ad libitum intake. The diet contained 16% crude protein. Blood samples were taken on the day prior to initiation of treatment (−1), on the first day of treatment (day 0), day 3, day 7, and day 14 of treatment. Samples were taken at −0.5, +0.25, +0.5, +1.0, +1.5, +2.0, +3.0, and +6.0 hours relative to the treatment injection and/or the a.m. feeding on each of the above days. Samples were assayed for glucose and insulin.

The averages of the samples taken on days 3 and 7 are shown in the following table. The data taken on day 0, which are omitted from the table, showed the expected short term increase in glucose and insulin levels that is characteristic of administration of phenethanolamines. The data taken on day 14 are omitted from the summary, because two pigs with particularly high glucose and insulin levels in the pGH treatment group quit eating. Since they were not eating, treatment was stopped and no blood samples were taken from these pigs on day 14. The data would have been skewed by the absence of these pigs' data. The remaining chronic treatment data (days 3 and 7) demonstrates that pGH, alone, significantly increased serum insulin and serum glucose levels. Ractopamine alone had no effect on serum glucose. However, when ractopamine was given in combination with pGH, ractopamine produced a chronic reduction in the hyperglycemic/hyperinsulinemic effect of pGH by itself.

The serum values given in the table are the means of the 8 samples taken at −0.5, +0.25, +0.5, +1.0, +1.5, +2.0, +3.0, and +6.0 hours each day. Day −1 was the day prior to initiation of treatments. The values for Days 3+7 are the averages of the samples taken after 3 days on treatment and 7 days on treatment combined.

|  | Glucose (mg/dl) | |
| --- | --- | --- |
|  | Day −1 | Days 3 and 7 |
| Control | 96.5 | 93.8 |
| pGH | 100.3 | 105.8 |
| ractopamine | 96.4 | 93.7 |
| ractopamine + pGH | 96.7 NS | 98.7* |

|  | insulin (microunits/ml) | |
| --- | --- | --- |
|  | Day −1 | Days 3 and 7 |
| Control | 28.1 | 28.8 |
| pGH | 38.8 | 53.9 |
| ractopamine | 27.0 | 19.6 |
| ractopamine + pGH | 32.1 NS | 30.2** |

NS Value not significantly different from value obtained with pGH administration alone.
*Value is significantly different (P < .06) from value obtained with pGH administration alone.
**Value is significantly different (P < .001) from value obtained with pGH administration alone.

The foregoing results confirm that ractopamine significantly reduces the hyperglycemic and hyperinsulinemic effect of pGH. The fact that two of the pigs receiving pGH treatment had particularly high glucose and insulin levels, quit eating, and had to be taken off of the experiment indicates the significance of the problem posed by elevated glucose and insulin levels.

We claim

1. A method for reducing an elevation of blood sugar or elevation of blood insulin, in a pig receiving an exogenous growth hormone related substance selected from the group consisting of growth hormone, growth hormone releasing factor, and analogues of growth hormone and growth hormone releasing factor, in an amount of from 0.5 to 10 mg/head/day, which comprises administering orally to the pig a diet containing ractopamine in a concentration of 1 to 30 ppm.

2. The method of claim 1 wherein the exogenous growth hormone related substance is porcine growth hormone, porcine growth hormone releasing factor, or an analogue of either.

3. The method of claim 2 wherein the exogenous growth hormone related substance is porcine growth hormone or an analogue.

4. The method of claim 3 wherein the porcine growth hormone or analogue is administered parenterally at a rate of 1.5 to 6.0 mg/head/day, and the ractopamine is administered in a diet at a concentration of 2.5 to 20 ppm.

5. The method of claim 2 wherein the exogenous growth hormone related substance is porcine growth hormone releasing factor or an analogue.

6. The method of claim 5 wherein the porcine growth hormone releasing factor or analogue is administered parenterally, and the ractopamine is administered in a diet at a concentration of 2.5 to 20 ppm.

7. A method for improving growth promotion and feed efficiency in a pig receiving both an exogenous growth hormone related substance selected from the group consisting of growth hormone, growth hormone releasing Factor, and analogues of growth hormone and growth hormone releasing factor, administered parenterally in an amount of from 0.5 to 10 mg/head/day, and a diet containing 20% or more crude protein which comprises administering orally to the pig a diet containing ractopamine in a concentration of 1 to 30 ppm.

8. The method of claim 7 wherein the exogenous growth hormone related substance is porcine growth hormone, porcine growth hormone releasing factor, or an analogue of either.

9. The method of claim 8 wherein the exogenous growth hormone related substance is porcine growth hormone or an analogue.

10. The method of claim 9 wherein the porcine growth hormone or analogue is administered parenterally at a rate of 1.5 to 6.0 mg/head/day, and the ractopamine is administered in a diet at a concentration of 2.5 to 20 ppm.

11. The method of claim 8 wherein the exogenous growth hormone related substance is porcine growth hormone releasing factor or an analogue.

12. The method of claim 11 wherein the porcine growth hormone releasing factor is administered parenterally and the ractopamine is administered in a diet at a concentration of 2.5 to 20 ppm.

* * * * *